United States Patent [19]
Tockman et al.

[11] Patent Number: 5,803,928
[45] Date of Patent: Sep. 8, 1998

[54] SIDE ACCESS "OVER THE WIRE" PACING LEAD

[75] Inventors: Bruce A. Tockman, Scandia; Bruce H. Kenknight, Maple Grove; Stuart R. Chastain, Shoreview; Randy W. Westlund, Minneapolis, all of Minn.

[73] Assignee: Cardiac Pacemakers, Inc., St. Paul, Minn.

[21] Appl. No.: 788,647

[22] Filed: Jan. 24, 1997

[51] Int. Cl.[6] .................................................. A61N 1/05
[52] U.S. Cl. ........................................ 607/122; 600/374
[58] Field of Search .................. 128/642; 607/122–128; 604/265; 600/373–375

[56] References Cited

U.S. PATENT DOCUMENTS

| | | |
|---|---|---|
| 4,000,745 | 1/1977 | Goldberg ................................ 607/122 |
| 4,351,345 | 9/1982 | Carney et al. .......................... 607/122 |
| 4,932,407 | 6/1990 | Williams . |
| 5,014,696 | 5/1991 | Mehra . |
| 5,099,838 | 3/1992 | Bardy . |
| 5,135,516 | 8/1992 | Sahatijian ............................... 604/265 |
| 5,304,218 | 4/1994 | Alferness ............................... 607/122 |
| 5,348,021 | 9/1994 | Adams et al. . |
| 5,350,404 | 9/1994 | Adams et al. . |
| 5,381,790 | 1/1995 | Kanesaka ............................ 607/125 X |
| 5,433,729 | 7/1995 | Adams et al. . |
| 5,458,621 | 10/1995 | White et al. . |
| 5,545,204 | 8/1996 | Cammilli et al. . |
| 5,643,231 | 7/1997 | Lurie et al. ........................ 607/122 X |
| 5,645,064 | 7/1997 | Littmann et al. ....................... 128/642 |

*Primary Examiner*—Jeffrey R. Jastrzab
*Attorney, Agent, or Firm*—Haugen and Nikolai, P.A.

[57] ABSTRACT

Intravenous cardiac leads having at least one electrode intended to be implanted within the coronary artery are disclosed. Also disclosed are structures and techniques for advancing such leads through the atrium and coronary sinus into the coronary veins overlaying the left ventricle.

46 Claims, 2 Drawing Sheets

SIDE ACCESS "OVER THE WIRE" PACING LEAD

BACKGROUND OF THE INVENTION

I. Field of the Invention

This invention relates to cardiac leads used in combination with a cardiac rhythm management device, e.g., heart pacemakers or defibrillators, to monitor and control the rhythm of the heart. This invention is more particularly directed toward lead configurations adapted to be implanted in the coronary veins on the left side of the heart and to methods for implanting such leads.

II. Discussion of the Prior Art

As explained in U.S. Pat. No. 4,928,688 to Morton M. Mower dated May 29, 1990, under normal circumstances impulses from the SA node affect contraction of the atria and then propagate to the AV node. The AV node then emits a second nerve impulse which affects contraction of the ventricles. In healthy individuals this is done in a coordinated manner to circulate blood through the body. However, many patients suffer from conditions which inhibit the transfer of nerve impulses from the SA node to the AV node and from there to the ventricles. In such cases, the chambers of the heart do not contract in a coordinated fashion and hemodynamic efficiency of the heart is decreased. This has profound adverse implications for the health and well-being of the patient. In minor cases, the quality of life is considerably reduced. More severe cases can result in death.

The Mower U.S. Pat. No. 4,928,688 patent describes a method for improving the hemodynamic efficiency of a sick heart. The method proposed in that patent is to place electrodes in both the right and left ventricles, monitor the cardiac signals originating in the right and left ventricles, analyze these signals and the absence thereof in a control circuit, and provide stimulating pulses to one or both ventricles within a time interval designed to improve the heart's hemodynamic efficiency.

Others have discussed the advantages of implanting leads in both the right and left ventricles to permit a sick heart to be more effectively defibrillated. See, for example, U.S. Pat. No. 4,922,407 to Williams; U.S. Pat. No. 5,099,838 to Bardy; and U.S. Pat. Nos. 5,348,021, 5,433,729, and 5,350,404 all to Adams et al. Each of the patents describe inserting a lead through the right atrium and coronary sinus into one of the coronary veins. None of these patents, however, discuss the difficulties encountered in doing so.

Important health advantages are achieved by positioning an electrode in a branch of the great vein of the heart. A lead so positioned can be used to stimulate the left ventricle. While it would be possible to position the electrode within the left ventricle, this can increase the potential for clot formation. If such a clot were released to the brain, the situation could be life threatening. However, traditional leads are not designed for implantation in this way. They tend to be too big. They also tend to have some type of fixation device that must be altered to advance the lead into the sinus. They also tend to require a stylet for positioning which is not flexible enough to permit such a lead to be implanted in the coronary vessels.

An arrangement intended to address such difficulties associated with the implantation of leads is disclosed in U.S. Pat. No. 5,304,218 granted to Clifton A. Alferness on Apr. 19, 1994. The arrangement disclosed in this patent includes a lead having an electrode. The electrode has a follower means for slidably engaging a guide wire. The electrode is implanted by feeding the guide wire along the desired path, engaging the follower means to the guide wire, advancing the lead along the guide wire until the electrode resides at the implant site, and retracting the guide wire from the follower means after the electrode is implanted at the implant site.

A review of the specification and drawings of U.S. Pat. No. 5,304,218 and an understanding of the anatomy and physiology of the heart demonstrates several problems with this approach. First, the path through which the lead must be fed is very restricted. The increased size of the distal end of the lead, given the presence of the follower, may make it more difficult to advance such a lead along the desired path so as to be positioned on myocardial tissue of the left ventricle. Second, the direction of blood flow through the veins tends to force electrodes implanted there out of the vein. This problem is likely to be exacerbated by the increase in the profile of the distal end given the presence of the follower. Third, the profile of the distal end of a lead implanted in a coronary vein may need to be made as small as possible to limit occlusion, limit damage to the vessels and myocardium and permit blood to flow as freely as possible through the blood vessel when the lead is in place.

SUMMARY OF THE INVENTION

The present invention provides an improved lead for implantation of an electrode into a coronary vein on the left side of the heart. The lead includes an elongated, flexible body member made of an electrically insulative material. The body member includes a proximal end and a distal end. A first lumen extends through the body member from the proximal end toward the distal end but does not reach the distal tip. A second lumen extends from the distal end so that the distal end includes an opening. This lumen exits the side of the lead prior to reaching the first lumen. The lead also includes a conductive member extending through the body member from the proximal end toward the distal end. Electrically coupled to the conductive member near its distal end is an electrode. Additional lumens, electrodes and conductive members may be included within and on the lead body.

Leads made in conformance with the present invention can be inserted in a number of different ways. For example, a guide catheter can be inserted and then the lead passed through the guide catheter until it is properly positioned. The guide catheter can then be retracted. The lead can be coated with a lubricious material to reduce friction between the lead and guide catheter. Similarly, a guide wire can be advanced to the implant site. Using the second lumen, the open distal end of the lead can be slid over the guide wire until the electrode is properly positioned. The guide wire can then be retracted.

Alternative embodiments of the present invention offer other advantages and features. For example, the wall of the lumen can be coated with PTFE to reduce friction between a guide wire and the wall of the lumen. The lumen can also be used to deploy a separate electrode past the distal end of the lead's body member. Additional lumens can be provided and the cross-section of the body member can be modified to provide a channel for a guide wire. These features are shown in the drawings and discussed in further detail below.

DETAILED DESCRIPTION OF THE INVENTION

Figure 1:
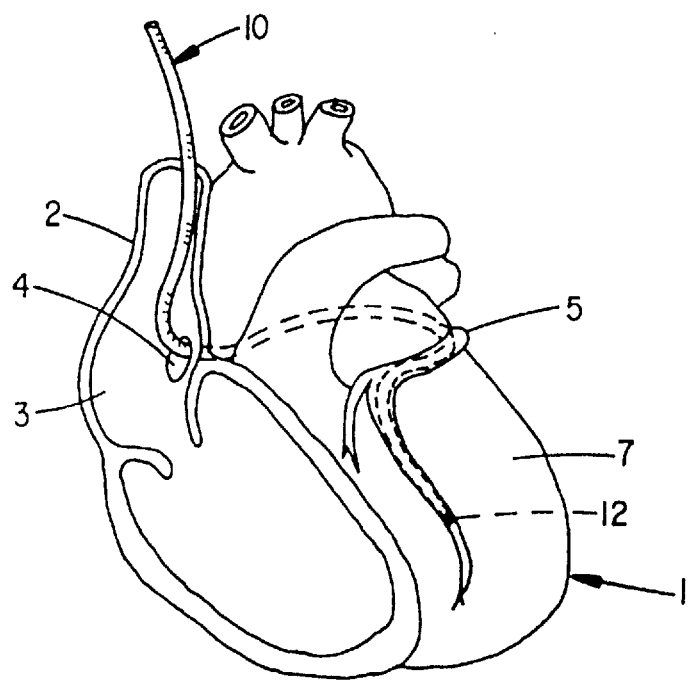
FIG. 1 is a plan view of an intravenous cardiac lead having an electrode positioned in a coronary vein.

FIG. 1 shows a human heart 1 with the intravenous coronary lead 10 of the present invention passing through the superior vena cava 2, the right atrium 3, and the coronary sinus 4 into the great vein of the heart 5 so that an electrode 12 on the lead 10 is implanted in a branch of the coronary vein. When positioned as shown, the electrode 12 can be used to sense the electrical activity of the heart or to apply a stimulating pulse to the left ventricle 7 and without the need of being in the left ventricular chamber.

Figure 2:
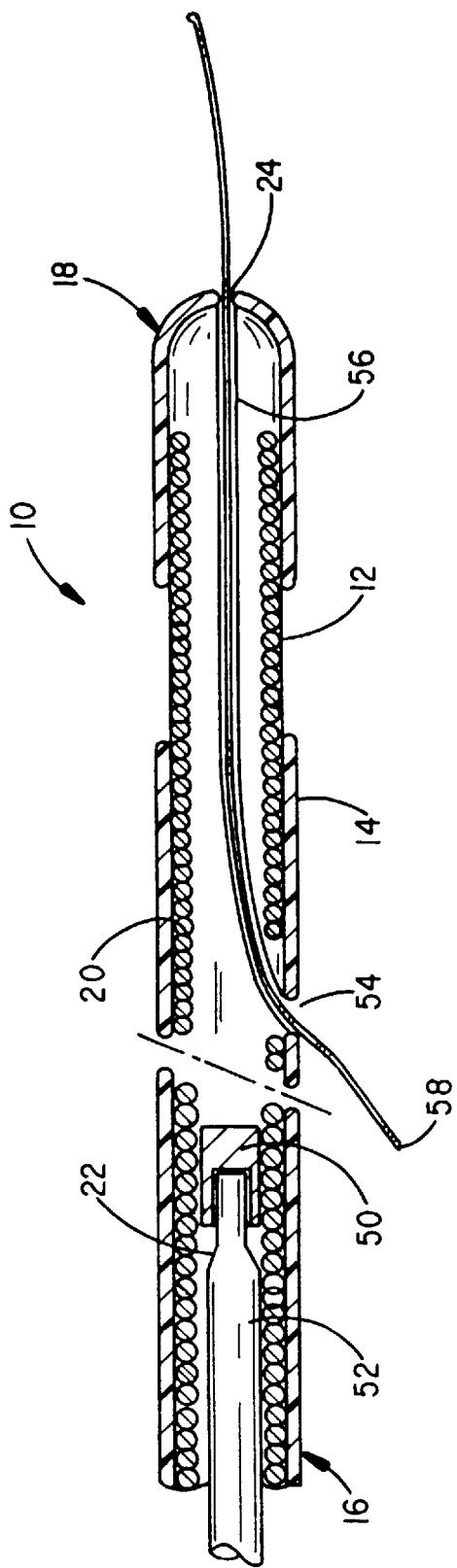
FIG. 2 is a longitudinal cross-section of a distal end portion of the present invention showing an intravenous coronary lead with a stylet stop and a lumen having a side entry port for insertion of a guide wire.

FIG. 2 shows in greater detail the structure of the intravenous coronary lead shown in FIG. 1. As shown in FIG. 2, the lead 10 includes an elongated body member 14 having a proximal end 16 and a distal end 18. The body member 14 is preferably made of a flexible, electrically insulative material. The outer surface of the body member 14 is preferably treated to prevent fibrotic attachment and to reduce inflammation response to the lead. Such a treatment could include a carbon coating, a steroid embedded in the material, a steroid eluting collar, or the like.

The body member 14 encapsulates a flexible electrically conductive member 20 extending from the proximal end 16 toward the distal end 18 of the lead's body member 14. Conductive member 20 is shown as a flexible wire coil in FIG. 2. Alternatively, the conductor member 20 could be in the form of a conductive wire, a thin ribbon, a plurality of fine wires formed as a cable, or a flexible tube without deviating from the invention.

The electrode 12 shown in FIG. 2 is preferably created by removing an annular portion of the insulative body member 14 to expose a portion of the underlying conductive member 20. When the conductive member 20 is a coil as shown in FIG. 2, the turns of the coil can be melt-banded such as by application of laser energy, to form the surface electrode 12. Those skilled in the art will recognize that either a ring electrode or a tip electrode electrically coupled to the conductive member 20 will also suffice.

Additional electrodes and conductors can be added for sensing, pacing or defibrillating as desired. For example, additional ring electrodes and a tip electrode with a central lumen can be added. Each such electrode should be coupled to an insulated conductive member running from the electrode through the body member 14 to the proximal end 16 of the body member so that these electrodes can be used to sense electrical activity in the heart or apply pacing or defibrillating pulses to the heart.

FIG. 2 also shows that the lead body member 14 includes a first lumen 22 extending from the proximal end 16 toward the distal end 18. A stop 50 is placed in the lumen 22 intermediate the proximal end 16 and distal end 18 a short predetermined distance from the distal end. A flexible stylet 52 can then be inserted into the lumen 22 through the proximal end of the lead body member 14 and advanced to engage the stop 50. The stylet 52 is used to push the lead forward and to apply torque to the lead. Slightly ahead of the stop 50, in the distal or tip section of the lead, is an orifice 54 through the side of the lead body member 14. This orifice 54 is shown to be in communication with a second lumen 56. Alternatively, orifice 54 can be used to provide another access to lumen 22 if the design is such that lumen 22 extends the length of the lead body member 14. In either case, the lumen extends toward the distal end 18 of the body member 14 and the orifice 54 and lumen cooperate to permit a guide wire 58 to be advanced through an opening 24 in the distal end 18 of the lead, the lumen and the orifice 54. The guide wire 58 can then be used to steer the lead 10 through the vasculature to the desired site for the electrode 12 while the stylet 52 is used to push the lead forward. Once the lead is in place, the guide wire 58 and stylet 52 are removed. Either lumen may be coated with a lubricious material. A polymer such as polytetrafluoroethylene (PTFE), for example, can coat the lumen to make it easier to insert or remove a guide wire or stylet.

While not shown in any of the views, leads of the prevent invention will have one or more connectors of a type known in the art at its proximal end for mating with the pacer and/or defibrillator pulse generator whereby depolarization signals originating in the heart can be sensed and stimulating pulses applied in accordance with the device's control algorithms.

The foregoing discussion is intended to illustrate various preferred arrangements for meeting the objections of the present invention. Modifications and variation can be made by those skilled in the art without departing from the invention. Accordingly, the invention is limited only by the scope of the following claims which are intended to cover all alternate embodiments and modifications as may fall within the true scope of this invention.

What is claimed:

1. For use with a cardiac rhythm management device, an intravenous lead having:
   (a) an elongated, flexible body member made of an electrically insulative material, said body member having a proximal end and distal end, said body member being sized to permit the distal end to be advanced through the right atrium and coronary sinus into the coronary veins;
   (b) a first opening in the body member at a point intermediate the proximal end and distal end of said body member;
   (c) a first lumen in communication with said first opening and extending toward the distal end of said body member;
   (d) a second lumen extending from said proximal end toward said first opening;
   (e) an electrode affixed to said body member;
   (f) a flexible coil-shaped electrically conductive member coupled to said electrode;
   (g) a stylet-engaging stop positioned in said second lumen between said first opening and said proximal end.

2. The lead defined by claim 1 having a second opening in said body member in communication with said first lumen.

3. The lead defined by claim 1 wherein said first lumen is coated with a lubricious material.

4. The lead defined by claim 1 wherein said conductive member extends through the body member from the proximal end toward the distal end of the body member.

5. The lead defined by claim 4 wherein said electrode is a ring electrode affixed to an outer surface of the body member.

6. The lead of claim 1 wherein the distal end portion of the body member tapers to a lesser diameter.

7. The lead of claim 1 wherein said first opening and said first lumen are sized to receive a guide wire therethrough.

8. The lead of claim 1 further including an opening at the proximal end of the body member in communication with said second lumen.

9. The lead of claim 8 wherein said opening at the proximal end of the body member and the portion of said second lumen proximal of said stop are sufficiently large to receive a stylet.

10. The lead of claim 1 further including a second lumen open to the proximal end of the body member.

11. The lead of claim 1 having an opening through the distal end of the body member in communication with said first lumen.

12. The lead of claim 10 wherein said lead has a coating of a lubricious material.

13. The lead of claim 10 wherein said first lumen and first opening are sized to receive a guide wire and said second lumen open to the proximal end of the body member is sized to receive a stylet.

14. The lead defined by claim 1 wherein said second lumen is coated with a lubricious material.

15. The lead of claim 1 wherein said body member is treated with an anti-inflammatory agent.

16. The lead of claim 1 wherein said lead body member is treated with an antifibrotic agent.

17. For use with a cardiac rhythm management device, an intravenous lead having:
 (a) an elongated, flexible body member made of an electrically insulative material, said body member having a proximal end and distal end, said body member being sized to permit the distal end to be advanced through the right atrium and coronary sinus into the coronary veins;
 (b) a first opening in the body member at a point intermediate the proximal end and distal end of said body member;
 (c) a first lumen in communication with said first opening and extending toward the distal end of said body member;
 (d) a second lumen extending from said proximal end toward said first opening;
 (e) an electrode affixed to said body member;
 (f) a flexible tube-shaped electrically conductive member coupled to said electrode;
 (g) a stylet-engaging stop positioned in said second lumen between said first opening and said proximal end.

18. The lead of claim 17 having a second opening in said body member in communication with said first lumen.

19. The lead defined by claim 17 wherein said first lumen is coated with a lubricious material.

20. The lead defined by claim 17 wherein said conductive member extends through the body member from the proximal end toward the distal end of the body member.

21. The lead defined by claim 20 wherein said electrode is formed by an opening in the body member exposing a portion of the conductive member.

22. The lead defined by claim 20 wherein said electrode is a ring electrode affixed to an outer surface of the body member.

23. The lead of claim 20 having an opening through the proximal end of the body member in communication with said second lumen.

24. The lead of claim 20 wherein said lead has a coating of a lubricious material.

25. The lead of claim 17 wherein the distal end portion of the body member tapers to a lesser diameter.

26. The lead of claim 17 wherein said first opening and said first lumen are sized to receive a guide wire therethrough.

27. The lead of claim 17 further including an opening at the proximal end of the body member in communication with said second lumen.

28. The lead of claim 17 wherein said first lumen and first opening are sized to receive a guidewire and said second lumen open to the proximal end of the body member is sized to receive a stylet.

29. The lead of claim 27 wherein said opening at the proximal end of the body member and the portion of said second lumen proximal of said stop are sufficiently large to receive a stylet.

30. The lead of claim 17 wherein said second lumen is open to the proximal end of the body member.

31. The lead defined by claim 17 wherein said second lumen is coated with a lubricious material.

32. The lead of claim 17 wherein said body member is treated with an anti-inflammatory agent.

33. The lead of claim 17 wherein said body member is treated with an antifibrotic agent.

34. For use with a cardiac rhythm management device, an intravenous lead having:
 (a) an elongated, flexible body member made of an electrically insulative material, said body member having a proximal end and distal end, said body member being sized to permit the distal end to be advanced through the right atrium and coronary sinus into the coronary veins;
 (b) a first opening in the body member at a point intermediate the proximal end and distal end of said body member;
 (c) a first lumen in communication with said first opening and extending toward the distal end of said body member;
 (d) a flexible electrically conductive member; and
 (e) an electrode comprising an opening in the body member exposing a portion of the flexible conductive member;
 (f) a second lumen extending from said proximal end toward said first opening and a second opening at the proximal end of the body member in communication with said second lumen, with a stylet-engaging stop within said second lumen located between said first opening and the proximal end.

35. The lead defined by claim 34 having a second opening in said body member in communication with said first lumen.

36. The lead defined by claim 34 wherein said first lumen is coated with a lubricious material.

37. The lead defined by claim 34 wherein said conductive member extends through the body member from the proximal end toward the distal end of the body member.

38. The lead defined by claim 37 wherein said conductive member is a coil.

39. The lead defined by claim 37 wherein said conductive member is a flexible tube.

40. The lead of claim 34 wherein the distal end portion of the body member tapers to a lesser diameter.

41. The lead of claim 34 wherein said first opening and said first lumen are sized to receive a guide wire therethrough.

42. The lead of claim 34 wherein said opening at the proximal end of the body member and the portion of said second lumen proximal of said stop are sufficiently large to receive a stylet.

43. The lead of claim 34 wherein said lead has a coating of a lubricious material.

44. The lead of claim 34 wherein said first lumen and first opening are sized to receive a guidewire and said second lumen open to the proximal end of the body member is sized to receive a stylet.

45. The lead of claim 34 wherein said body member is treated with an anti-inflammatory agent.

46. The lead of claim 34 wherein said body member is treated with an antifibrotic agent.

* * * * *

UNITED STATES PATENT AND TRADEMARK OFFICE
CERTIFICATE OF CORRECTION

PATENT NO. : 5,803,928
DATED : September 8, 1998
INVENTOR(S) : Bruce H. Tockman, et al It is certified that error appears in the above-indentified patent and that said Letters Patent is hereby corrected as shown below:

Claim 16, column 5, line 17 "lead" should be deleted.

Claim 28, column 5, line 66 "17" should be -- 27 --.

Claim 34, column 6, line 27 after "member;" delete "and"; same claim, line 30 after "member;" insert -- and --.

Signed and Sealed this

Second Day of February, 1999

Attest:

Attesting Officer

*Acting Commissioner of Patents and Trademarks*